United States Patent
Xu et al.

(10) Patent No.: US 9,390,483 B2
(45) Date of Patent: Jul. 12, 2016

(54) PROCESSING METHOD OF PRESSURE-SENSITIVE LIGHT AND SHADOW IMAGING SYSTEM AND FORMED FOOTPRINT IMAGE

(71) Applicant: DALIAN EVERSPRY SCI & TECH CO., LTD., Liaoning (CN)

(72) Inventors: Xu Xu, Liaoning (CN); Guojian Wang, Liaoning (CN); Zhongjian Tan, Liaoning (CN)

( * ) Notice: Subject to any disclaimer, the term of this patent is extended or adjusted under 35 U.S.C. 154(b) by 127 days.

(21) Appl. No.: 14/362,921

(22) PCT Filed: Dec. 26, 2012

(86) PCT No.: PCT/CN2012/087537
§ 371 (c)(1),
(2) Date: Jun. 5, 2014

(87) PCT Pub. No.: WO2014/101003
PCT Pub. Date: Jul. 3, 2014

(65) Prior Publication Data
US 2015/0254821 A1    Sep. 10, 2015

(51) Int. Cl.
| | |
|---|---|
| G06K 9/00 | (2006.01) |
| G06T 5/00 | (2006.01) |
| A61B 5/117 | (2016.01) |
| A43D 1/08 | (2006.01) |
| G06K 9/20 | (2006.01) |
| A43D 1/02 | (2006.01) |
| G06K 9/58 | (2006.01) |
| G06T 11/00 | (2006.01) |
| H04N 5/235 | (2006.01) |
| G06F 3/041 | (2006.01) |

(52) U.S. Cl.
CPC . *G06T 5/008* (2013.01); *A43D 1/02* (2013.01); *A43D 1/08* (2013.01); *A61B 5/1174* (2013.01); *G06F 3/0414* (2013.01); *G06K 9/00637* (2013.01); *G06K 9/20* (2013.01); *G06K 9/58* (2013.01); *G06T 5/002* (2013.01); *G06T 5/003* (2013.01); *G06T 11/001* (2013.01); *H04N 5/2355* (2013.01); *G06T 2207/10004* (2013.01); *G06T 2207/20182* (2013.01); *G06T 2207/20208* (2013.01)

(58) Field of Classification Search
CPC ......... A43D 1/02; A43D 1/08; A61B 5/1174; G06K 9/00637; G06K 9/20; G06K 9/58; G06T 11/001; G06T 5/002; G06T 5/003; G06T 5/008; G06T 2207/10004; G06T 2207/20182; G06T 2207/20208; H04N 5/2355
See application file for complete search history.

(56) References Cited

FOREIGN PATENT DOCUMENTS

| CN | 101874738 | * | 11/2010 | ......... G06K 9/00362 |
|---|---|---|---|---|
| JP | 2002-123822 | * | 4/2002 | ............. A61B 5/117 |

*Primary Examiner* — Amara Abdi
(74) *Attorney, Agent, or Firm* — Prakash Nama; Global IP Services, PLLC

(57) ABSTRACT

The pressure-sensitive light and shadow imaging system is comprised of carrier medium (1), inductive surface (2), photo source (3), photocell (5) and imaging surface (6), wherein the said carrier medium (1) is set on the top of the pressure-sensitive light and shadow imaging system, and the lower end contacts with the inductive surface (2) whose lower end is closely integrated with upper surface of the photocell (5). The imaging surface (6) is set underneath the photocell (5). Texture substance (7) contacts the carrier medium (1), which can form the pressure-sensitive image. The image can reflect the pressure distribution of the substance and compression sequence. With the processing method of footprint image formed by such pressure-sensitive light and shadow imaging system, several single-frame footprint images are processed as a complete footprint image containing all footprint features, which can eliminate background noise.

18 Claims, 6 Drawing Sheets

(a) (b)

(c) (d)

(e)

(a)

(b)

PROCESSING METHOD OF PRESSURE-SENSITIVE LIGHT AND SHADOW IMAGING SYSTEM AND FORMED FOOTPRINT IMAGE

BACKGROUND OF THE INVENTION

The present invention relates to the image processing, in particular to a processing method of pressure-sensitive light and shadow imaging system and formed footprint image.

The existing imaging system is based on the light ray reflected by the object, and the formed image is dimensional, and the size of pressure can't be observed on the displayed plane picture. The pressure distribution of texture substance, e.g. footprint image, plays a critical role in the criminal investigation.

With the development of existing technology, the handwriting electronic imaging system is also highly developed, but the handwritings can only be displayed on electronic equipment with existing technology, and its pressure distribution and stroke order can't be inquired and saved. The stroke order and pressure distribution are mainly studied to identify handwritings in the handwriting comparison system and handwriting inquiry system.

Now, the static picture shoot by camera directly and subsequent digital processing are available for collecting the footprint patterns, but the disadvantages of such processing mode are that the footprint image obtained is incomplete, and the heel and toe images are insufficient or incorrect. The other method to collect footprint pattern is to first acquire footprint, take pictures or scan, and finally execute digital processing, but the disadvantages of such method are that additional materials required for stamp are required, and the digitalized footprint image is available through several steps. Therefore, in most cases, the relatively advanced footprint collection instrument is adopted to collect the footprint image which is shoot by camera and saved to a series of single-frame images. A series of single-frame images are integrated into a complete footprint image, which can digitalize rapidly and directly, and save the materials required for stamped footprint and the time of converting the stamped footprint into digital footprint.

It shall make the rear foot (barefoot or with socks or shoes) first contact the collection instrument, put down the middle to make it contact the collection instrument and finally lift heel to make the forefoot contact the collection instrument so as to get a complete footprint image when the flat image information of footprint is collected with footprint collection instrument. During the whole process, the contact site of sole and collection instrument is from rear foot to forefoot gradually. The footprint image collected by collection instrument is a multi-frame image, and only a part of footprint image is displayed on each frame image. Based on the need of footprint digitalization, such multi-frame image must be integrated into a complete footprint image.

The noise interference is present on the data background of footprint collection instrument after a long time due to external factors, so that the footprint image collected contain noise.

BRIEF SUMMARY OF THE INVENTION

The purpose of the present invention is to provide a pressure-sensitive light and shadow imaging system which can collect the formed image of texture substance, and make the formed image reflect the pressure distribution and compression subsequence.

Another purpose of the present invention is to provide a footprint image processing method which can process the single-frame footprint image as a complete footprint image containing all footprint features, and eliminate the background noise in the complete footprint image to form an image only containing complete footprints.

For this purpose, the technical solution of the invention is as follows: a pressure-sensitive light and shadow imaging system, including the carrier medium bearing the pressure of texture substance, photocell, light source, inductive surface and imaging surface, characterized in that the said carrier medium is set on the top of pressure-sensitive light and shadow imaging system, and its lower surface contacts with inductive surface whose lower surface closely contact with the upper surface of photocell. The imaging surface is set underneath the light and shadow system, and the light source is set on at least one side of photocell.

The said texture substance refers to a sole, fingerprint or handwriting.

The said carrier medium is a plane substance which at least includes a synthetic fiber layer, and the said preferable synthetic fiber layer is one of or a combination of polypropylene, orlon, vinylon, nylon and dacron.

The said plane substance also includes an elastic composite layer and is of reflection. The said elastic composite layer is of elastic rubber, and the said preferable elastic rubber is one of or a combination of silica gel, natural rubber, polyurethane, polystyrene or polyolefin.

The said inductive surface is a transparent film with a certain elasticity and thickness. The refractive index of said transparent film is similar to that of photocell, and the said transparent film reflects the light on the supper surface of photocell and inducts the pressure distribution of texture substance at different locations. The said inductive surface (2) is an elastic rubber transparent film, and the said preferable elastic rubber is one of or a combination of silicone rubber, natural rubber, polyurethane, polystyrene or polyolefin, and the said most preferable polystyrene or polyolefin is SBS, SIS, SEBS, SEPS, EPR, NBR or HR.

The tensile strength, elongation (%), bending strength and modulus of elasticity of elastic rubber transparent film of the said inductive surface (2) are 0.08 Mpa~10 Mpa, 150~700, 0.1-20 Mpa and less than 8 Mpa respectively.

The photocell is a plane optical body with a certain thickness, and the said light source is evenly set on the side of photocell. The LED white light source with color temperature of 6000K-7000K is preferred, and the said imaging surface is a horizontal or diagonal reflective mirror.

The imaging method of a pressure-sensitive light and shadow imaging system includes the following steps:

A The texture substance to be imaged is put on the upper surface of carrier medium which will transmit the pressure to the inductive surface;

B The inductive surface will induct the pressure distribution of texture surface, and the tightness between inductive surface and carrier medium is reflected by the reflection of light ray in photocell through inductive surface so as to form the pressure distribution image of texture substance.

C The inductive surface projects the pressure distribution image of texture substance on the imaging surface.

In the said step B, the inductive surface closely contact with the lower surface of pressed carrier medium, and the light ray reflected by inductive surface with optical properties is projected to the imaging surface through photocell; the image collection instrument is set at the corresponding location of imaging surface so as to collect the texture substance image into the computer, so that the computer can convert the collected black-and-white image into a pseudo-color image which can display pressure distribution or binary image with texture features.

A processing method of footprint image formed by pressure-sensitive light and shadow imaging system, including the following processes:

1) Save a background image containing noise;
2) Select a footprint image from current footprint image library as the target partial footprint image to protect footprint image or establish a frame blank image as the target partial footprint image to protect footprint image;
3) Select an unprocessed image from current footprint image library as the source partial footprint image;
4) Overlap and process the source and target partial footprint images;
5) Take the overlapped and processed footprint image as new target partial footprint image;
6) Repeat steps 3-6 until all footprint images are overlapped, i.e. all images in current footprint image library are fully overlapped to obtain the complete footprint image containing noise is obtained.
7) Calculate the complete footprint image and the background image saved in step 1) to obtain a complete footprint image without noise.

The said footprint image is collected by pressure-sensitive imaging footprint collection system, and the heel first contacts the footprint collection system. It shall put down the middle of sole and lift heel so that the toe can contact the footprint collection instrument. The footprint image between heel and toe is collected in order, and only part of footprints is displayed on footprint image of each frame.

The background image as claimed in step 1) is a single-frame image without footprint on the imaging surface of pressure-sensitive imaging footprint collection system before the footprint image is collected.

The target image as claimed in step 2) is a footprint image collected by footprint collection system or a blank image established, and the footprint image with larger footprint is preferred.

The unprocessed footprint image as claimed in step 3) is a footprint image in the footprint image library, and the said source image is a footprint image other than target image.

The overlapping steps as claimed in step 4) are as follows:

Subtract the source partial footprint image from the target partial footprint image, and enter the location of the point where the gray difference $d_{(i,j)}$ of pixel is greater than 0 into the library;

Replace the gray value of target partial footprint image at (i,j) with the gray value of source partial footprint image at the same location as the gray value of target footprint image at (i,j), and obtain the overlapped target partial footprint image.

In the said (i,j), i is the number of rows of image pixel, j is the number of columns of image pixel.

The operation as claimed in step 7) is the subtraction.

The said subtraction is as follows:

The gray value of noiseless complete target footprint image pixel at (x, y) is the gray value of target complete footprint image pixel at (x, y) minus the gray value of background image pixel at (x, y), until the gray values of all pixels are subtracted.

Compared with the prior art, the invention has the following advantages:

The invention relates to an image formed by pressure-sensitive light and shadow imaging system, which can reflect the image with substance texture, pressure distribution of the substance and compression sequence.

The invention relates to a processing method of footprint image formed by pressure-sensitive light and shadow imaging system, and only the footprints in the overlapped image are overlapped into the target footprint image.

The invention relates to a processing method of footprint image formed by pressure-sensitive light and shadow imaging system, and no background noise is contained in the footprint image after processing without affecting the identification of footprint and subsequent operation.

DETAILED DESCRIPTION OF THE INVENTION

Figure 1:
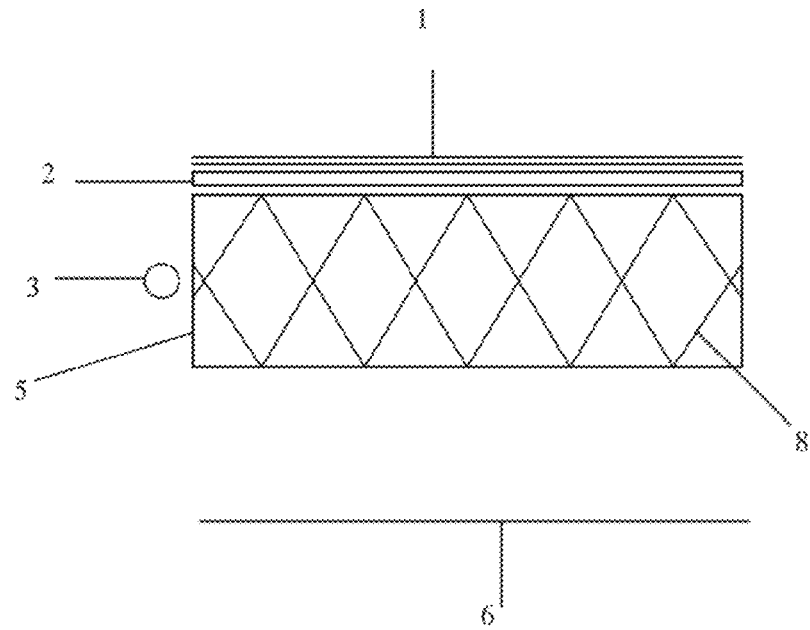
FIG. 1 Schematic View of the Invention.

A pressure-sensitive light and shadow imaging system of the invention is described in detail in combination with the attached drawings:

A pressure-sensitive light and shadow imaging system as shown in FIG. 1, including the carrier medium 1 bearing the pressure of texture substance 7, photocell 5, light source 3, inductive surface 2 and imaging surface 6, characterized in that the said carrier medium 1 is set on the top of pressure-sensitive light and shadow imaging system, and its lower surface contacts with inductive surface 2 whose lower surface closely contact with the upper surface of photocell 5. The imaging surface 6 is set underneath the light and shadow system, and the light source 3 is set on at least one side of photocell 5.

The said texture substance 7 refers to a sole, fingerprint or handwriting.

The said carrier medium 1 is a plane substance which at least includes a synthetic fiber layer, and the said preferable synthetic fiber layer is one of or a combination of polypropylene, orlon, vinylon, nylon and dacron, and the said optimal synthetic fiber layer is nylon and Dacron.

The said plane substance also includes an elastic composite layer and is of reflection. The said elastic composite layer is of elastic rubber, and the said preferable elastic rubber is one of or a combination of silica gel, natural rubber, polyurethane, polystyrene or polyolefin, and the said most preferable elastic rubber is silica gel and polyurethane.

The carrier medium 1 is a thin film plane substance with fine and flexible properties. The carrier medium is a thin film with fine and flexible properties, which can ensure the carrier medium won't crack under high pressure. Moreover, the fine property can better reflect the texture features of such substance. The elastic composite layer will deform under pressure, and the contact tightness with the inductive surface varies with the pressure, i.e. the carrier medium in the texture area with high pressure closely contacts with the inductive surface. On the contrary, the carrier medium in the texture area with relatively low pressure loosely contacts with the inductive surface.

The said inductive surface 2 is a transparent film with a certain elasticity and thickness. The refractive index of said transparent film is similar to that of photocell 5, and the said transparent film reflects the light on the supper surface of photocell and inducts the pressure distribution of texture substance at different locations. The said inductive surface 2 is an elastic rubber transparent film, and the said preferable elastic rubber is one of or a combination of silicone rubber, natural rubber, polyurethane, polystyrene or polyolefin, and the said more preferable polystyrene or polyolefin is SBS, SIS, SEBS, SEPS, EPR, NBR or IIR, and the most preferable elastic rubber is silicone rubber or polyurethane.

The tensile strength, elongation (%), bending strength and modulus of elasticity of elastic rubber transparent film of the said inductive surface 2 are 0.08 Mpa~10 Mpa, 150~700, 0.1-20 Mpa and less than 8 Mpa respectively.

The photocell 5 is a plane optical body with a certain thickness, which can penetrate through light ray and refracted ray, and the light source 3 is evenly set on the side of photocell 5. The LED white light source with color temperature of 6000K-7000K is preferred for the reason that the spectrum of such light source is stable and durable, and the light source is set on the side of optical body, so when the texture substance is larger, the imaging quality can be greatly improved by adding the light source, e.g. a same light source is added on the side opposite to the light source, or the light source are set on four sides of optical glass.

The imaging surface 6 is a horizontal or diagonal reflective mirror, and the image collection equipment is provided at the opposite side of corresponding horizontal or diagonal imaging surface.

The imaging method of a pressure-sensitive light and shadow imaging system includes the following steps:

A The texture substance 7 to be imaged is put on the upper surface of carrier medium 1 which will transmit the pressure to the inductive surface 2;

B The inductive surface 2 will induct the pressure distribution of texture surface, and the tightness between inductive surface 2 and carrier medium 1 is reflected by the reflection of light ray in photocell through inductive surface 2 so as to form the pressure distribution image of texture substance 7.

C The inductive surface 2 projects the pressure distribution image of texture substance on the imaging surface 6.

In the said step B, the inductive surface closely contact with the lower surface of pressed carrier medium, and the light ray reflected by inductive surface with optical properties is projected to the imaging surface through photocell; the image collection instrument is set at the corresponding location of imaging surface so as to collect the texture substance image into the computer, so that the computer can convert the collected black-and-white image into a pseudo-color image which can display pressure distribution or binary image with texture features.

The invention can be used in footprint collection system, and the suspect stamps on the cattier medium 1 for the reason that the carrier medium will transfer the pressure distribution and texture features at different locations to the transparent reflective film with a certain elasticity and thickness of inductive surface 2 through shoe sole pattern (i.e. texture). Such reflective film is sensitive, so the tightness with each part of photocell varies due to the difference of pressure and the existence of texture, which therefore various images will be displayed on the imaging surface under the act of light sensitive system. When the carrier medium 1 is of elastic composite layer, the effect on footprint will be further reflected by the fineness difference between elastic composite layer and inductive layer 2 under difference pressure so as to meet footprint imaging requirements.

The images on the imaging surface are collected into the computer through other image collection instrument, e.g. camera, so as to manually analyze whether the pressure distribution of footprint is identical with that on the site.

The contact tightness between the stroke trace of Chinese characters or other characters and the photocell is recorded on the imaging surface with the deformation of reflective film by writing on the carrier medium of the Invention, and the stroke order and force are also recorded.

The footprint image adopted in the embodiment is collected by pressure-sensitive imaging footprint collection system, and the heel first contacts the footprint collection system. It shall put down the middle of sole and lift heel so that the toe can contact the footprint collection instrument. The footprint image between heel and toe is collected in order, and only part of footprints is displayed on footprint image of each frame.

Figure 3:
FIG. 3 Footprint Image Collected by the System of the Invention.

A processing method of footprint image formed by pressure-sensitive light and shadow imaging system, including the following processes:

1) Save a background image containing noise as shown in FIG. 3a, i.e. an image containing background noise is separately collected as the background image before the footprint image is collected.

Figure 2:
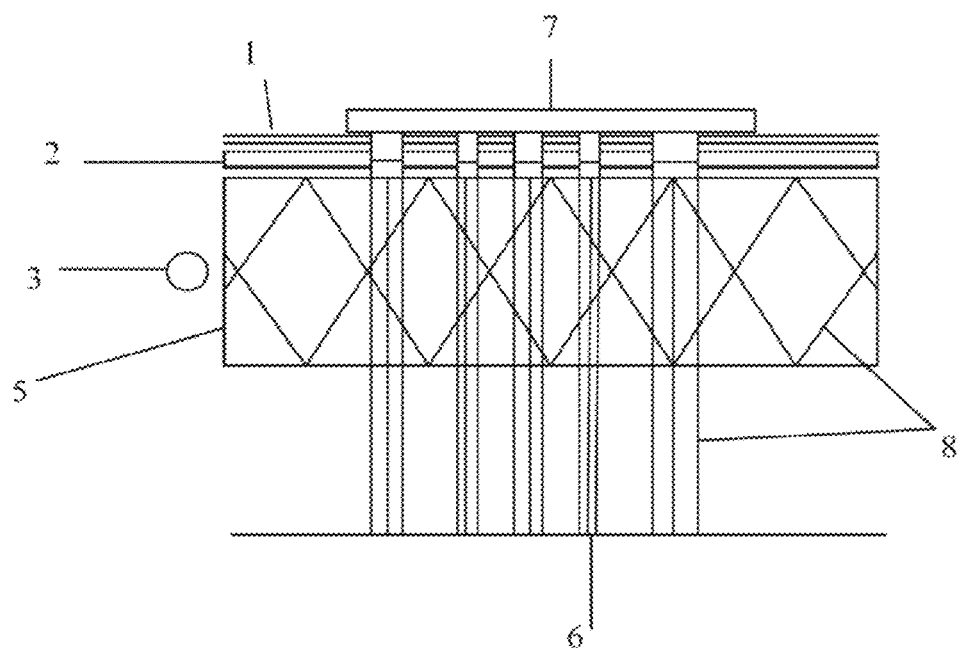
FIG. 2 Imaging diagram of pressure-sensitive light and shadow imaging system of the invention by applying texture substance.

2) Save the collected footprint image into the footprint image library as shown in FIGS. 2a, b, c, d and e, i.e. select an image from current footprint image library as the target partial footprint image which can be any footprint image or establish a frame blank image as the target footprint image. An image with larger footprint in the footprint image is preferred as the target partial footprint image as shown in FIG. 2a, which can save the calculation time.

3) Select an image from current footprint image library as the source partial footprint image which can be any footprint image as shown in FIG. 2b;

4) Overlap the source and target partial footprint images;

The source partial footprint image is subtracted from target partial footprint image, i.e. the difference value $d_{(i,j)}$ is the gray value of pixel minus that of pixel at same location (a, b) (a and b represent the number of rows and lines of pixel respectively), and the location (i,j) of the point where the gray difference $d_{(i,j)}$ of pixel is greater than 0 is saved into the database;

The gray value of target partial footprint image at (i,j) is replaced with the gray value of source partial footprint image at the same location as the gray value of target footprint image at (i,j), and the target partial footprint image overlapped is obtained after all the points where the gray difference $d_{(i,j)}$ of pixel is greater than 0. In the said (i,j), i is the number of rows of image pixel, j is the number of columns of image pixel.

5) Take the overlapped footprint image in step 4) as the new target partial footprint image;

6) Repeat steps 3-5 until all partial footprint images are overlapped, i.e. all images in current footprint image library are fully overlapped to obtain the complete footprint image containing noise as shown in FIG. 3b.

7) Calculate the complete footprint image and the background image saved in step 1) as shown in FIG. 3a to obtain a complete footprint image without noise.

Figure 4:
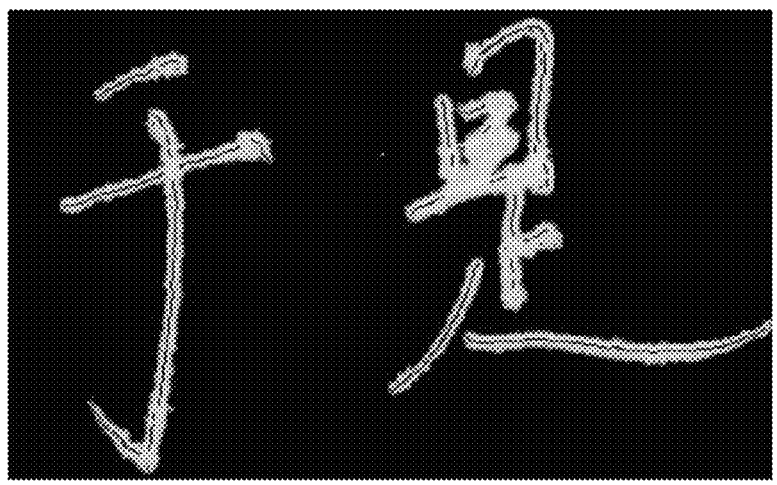
FIG. 4 Stroke image collected by the system of the invention.
Figure 5:
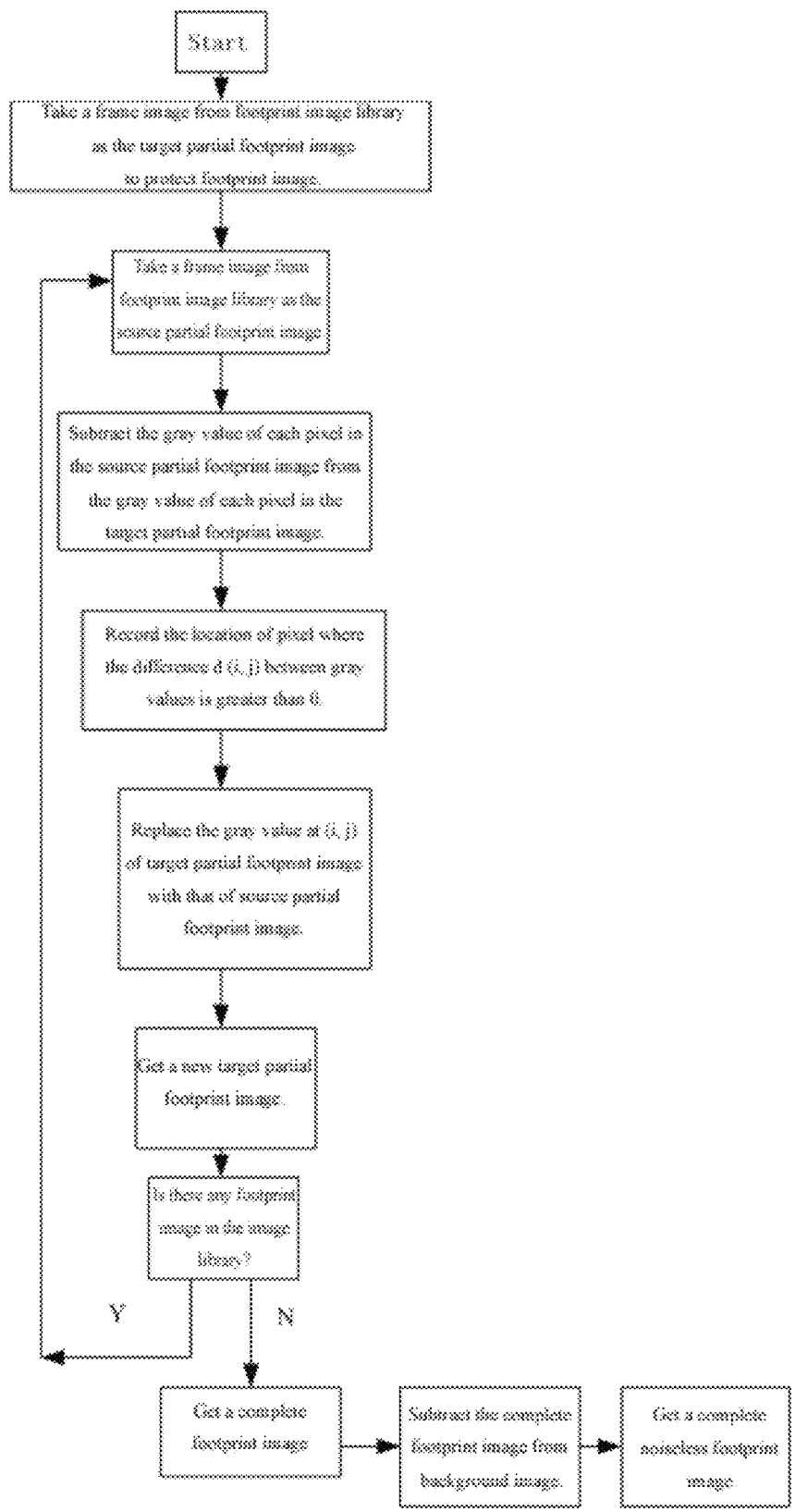
FIG. 5 Flow Chart of a Footprint Image Processing Method of the Invention.
Figure 6:
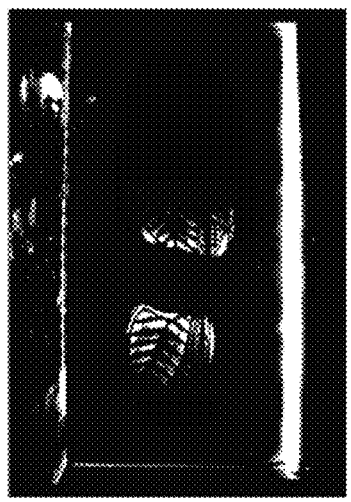
FIG. 6 Single-frame partial footprint image containing noise collected by footprint collection instruments a, b, c, d and e.
Figure 6:
Figure 6:
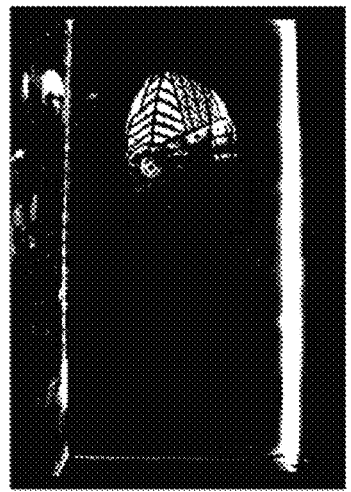
Figure 6:
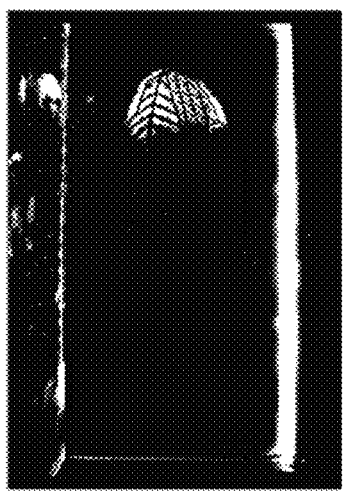
Figure 6:
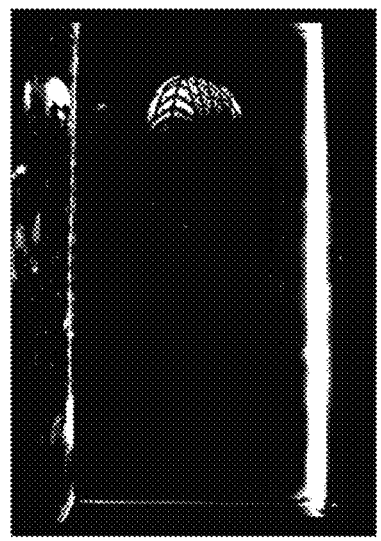
Figure 7:
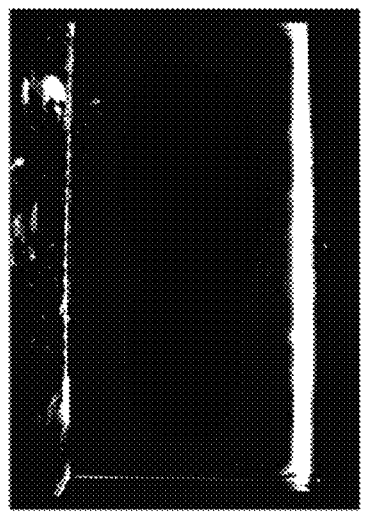
FIG. 7a Background Image Collected by Footprint Collection Instrument.
FIG. 7b Complete footprint image containing noise after overlapping and processing.
Figure 7:
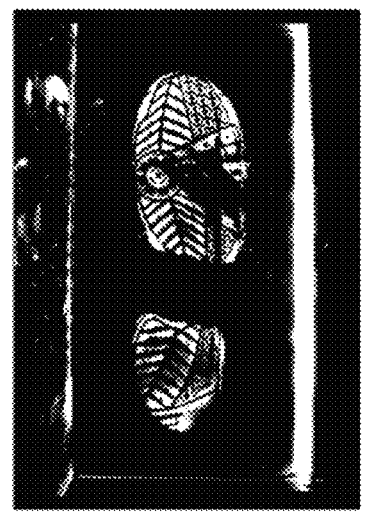
Figure 8:
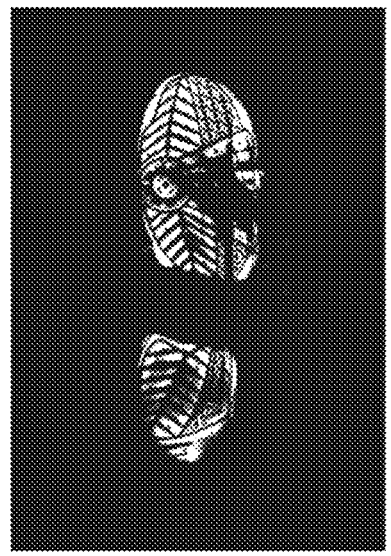
FIG. 8 Noiseless complete footprint image.
1 Carrier medium 2. Inductive surface 3. Light source 5. Photocell 6. Imaging surface 7. Texture substance 8. Light ray

The subtraction as claimed in step 7) is as follows:

The gray value of noiseless complete target footprint image pixel at (x, y) is the gray value of target complete footprint image (as shown in FIG. 3b) pixel at (x, y) minus the gray value of background image (as shown in FIG. 3a) pixel at (x, y), until the gray values of all pixels are subtracted to obtain the noiseless footprint image as shown in FIG. 4.

As described above, the similar technical solution can be derived in combination with the drawings and embodiments. Thus, any technical solution of the present invention without departing from the contents of the technical substance according to the invention the above embodiments made any simple modifications, equivalents, changes and modifications are still a technical solution of the invention within the scope of protection.

What is claimed is:

1. A pressure-sensitive light and shadow imaging system, including a carrier medium bearing pressure of a texture substance, a photocell, a light source, an inductive surface and an imaging surface, characterized in that the carrier medium is set as an uppermost layer of the pressure-sensitive light and shadow imaging system, the carrier medium is a plane substance comprising a synthetic fiber layer and an elastic composite layer; a lower surface of the carrier medium contacts with the inductive surface; the inductive surface is thicker than the elastic composite layer, a lower surface of the inductive surface closely contacts with an upper surface of the photocell; the imaging surface is set underneath the pressure-sensitive light and shadow imaging system, and the light source is set on at least one side of the photocell.

2. The pressure-sensitive light and shadow imaging system according to claim 1, characterized in that the texture substance is a sole, fingerprint or handwriting.

3. The pressure-sensitive light and shadow imaging system according to claim 1, characterized in that the synthetic fiber layer is one of or a combination of polypropylene, orlon, vinylon, nylon and dacron.

4. The pressure-sensitive light and shadow imaging system according to claim 1, characterized in that the elastic composite layer is made of elastic rubber, and the elastic rubber is one of or a combination of silica gel, natural rubber, polyurethane, polystyrene or polyolefin.

5. The pressure-sensitive light and shadow imaging system according to claim 1, characterized in that the inductive surface is a transparent film with a certain elasticity and thickness; a refractive index of said transparent film is similar to that of the photocell, and the transparent film reflects lights on the upper surface of the photocell and inducts pressure distribution of the texture substance at different locations.

6. The pressure-sensitive light and shadow imaging system according to claim 5, characterized in that the said inductive surface is an elastic rubber transparent film, and the elastic rubber is one of or a combination of silicone rubber, natural rubber, polyurethane, polystyrene or polyolefin, and the said polystyrene or polyolefin is SBS, SIS, SEBS, SEPS, EPR, NBR or IIR.

7. The pressure-sensitive light and shadow imaging system according to claim 6, characterized in that the tensile strength, elongation (%), bending strength and modulus of elasticity of the elastic rubber transparent film of the said inductive surface are 0.08 Mpa.about.18 Mpa, 150.about.700, 0.1-20 Mpa and less than 8 Mpa respectively.

8. The pressure-sensitive light and shadow imaging system according to claim 1, characterized in that the photocell is a plane optical body with a certain thickness, and the said light source is evenly set on at least one side of photocell. The light source is an LED white light source with color temperature of 6000K-7000K, and the imaging surface is a horizontal or diagonal reflective mirror.

9. An imaging method employed by the pressure-sensitive light and shadow imaging system as claimed in claim 1, characterized in that the imaging method comprises the following steps:
   A. put the texture substance to be imaged on an upper surface of the carrier medium which will then transmit pressure of the texture substance to the inductive surface;
   B. the inductive surface including pressure distribution of the texture substance, and tightness between the inductive surface and the carrier medium is reflected by reflection of light ray in the photocell through the inductive surface to form a pressure distribution image of the texture substance;
   C. the inductive surface projecting the pressure distribution image of the texture substance on the imaging surface.

10. The imaging method according to claim 9, characterized in that in said step B, the inductive surface closely contacts with a lower surface of the carrier medium, and the light ray reflected by inductive surface with optical properties is projected to the imaging surface through photocell; an image collection instrument is set at location corresponding to the imaging surface to collect the pressure distribution image into the computer, the computer then converts the collected pressure distribution image in black-and-white into a pseudo-color image which can display pressure distribution or a binary image with texture features.

11. A processing method of footprint images forme by the pressure-sensitive light and shadow imaging system as claimed in claim 1, characterized in that the processing method of footprint images comprises the following processes:
   1) save a background image containing noise;
   2) select one of the footprint images from a current footprint image library as a target partial footprint image or establish a frame blank image as the target partial footprint image;
   3) select another unprocessed footprint image from the current footprint image library as a source partial footprint image;
   4) overlap the source partial footprint image and the target partial footprint image to obtain an overlapped and processed footprint image;
   5) take the overlapped and processed footprint image as a new target partial footprint image;
   6) repeat steps 3-5 until all footprint images the current footprint image library are fully overlapped to obtain a complete footprint image containing noise;
   7) calculate the complete footprint image containing noise and the background image containing noise saved in step 1) to obtain a complete footprint image without noise; wherein the footprint images are collected through a pressure-sensitive imaging footprint collection system by firstly contacting a heel of a foot with the pressure-sensitive imaging footprint collection system, and then putting down a middle part of the foot and lifting the heel for a toe of the foot to contact a footprint collection instrument of the pressure-sensitive imaging footprint collection system; the footprint images between the heel and the toe are collected in order, and only part of a complete footprint is displayed on each of the footprint images.

12. The processing method of footprint image according to claim 11, characterized in that the background image containing noise is a single-frame image without footprint on an imaging surface of the pressure-sensitive imaging footprint collection system before the footprint images are collected.

13. The processing method of footprint image according to claim 11, characterized in that the target partial footprint image is a footprint image collected by the pressure-sensitive imaging footprint collection system or the frame blank image is established.

14. The processing method of footprint image according to claim 11, characterized in that the unprocessed footprint image is a footprint image in the footprint image library, and the source partial footprint image is a footprint image other than the target partial footprint image.

15. The processing method of footprint image according to claim pall, characterized in that overlapping the source partial footprint image and the target partial footprint image, to obtain the overlapped and processed footprint image in step 4 comprises the following steps:
  subtract the source partial footprint image from the target partial footprint image, enter a location of a point where the gray difference $d_{ij}$ of pixel is greater than 0 into the footprint image library;
  replace gray value of the target partial footprint image at (i,j) with gray value of the source partial footprint image at the same location as the gray value of the target footprint image at (i,j), and obtain the overlapped and processed footprint image.

16. The processing method of footprint image according to claim 15, characterized in that in said (i,j), i is a number of rows of image pixel, j is a number of columns of image pixel.

17. The processing method of footprint image according to claim 16, characterized in that subtraction is performed to calculate the complete footprint image containing noise and the background image containing noise in step 7.

18. The processing method of footprint image according to claim 17, characterized in that said subtraction is as follows: a gray value of noiseless complete target footprint image pixel at (x, y) is a gray value of target complete footprint image pixel at (x, y) minus a gray value of background image pixel at (x, y), until the gray values of all pixels are subtracted.

* * * * *